United States Patent
Glover

[11] Patent Number: 5,466,456
[45] Date of Patent: Nov. 14, 1995

[54] FACIAL CLEANSER

[76] Inventor: Morris S. Glover, 6033 Bear Creek Dr., Apt. 104, Bedford Heights, Ohio 44046

[21] Appl. No.: 90,565

[22] Filed: Jul. 12, 1993

Related U.S. Application Data

[63] Continuation of Ser. No. 800,600, Nov. 27, 1991, abandoned.

[51] Int. Cl.$^6$ ............................. A61K 7/00; A61K 9/70
[52] U.S. Cl. ..................... 424/401; 424/497; 514/859; 606/131
[58] Field of Search ..................... 606/131; 602/58; 424/401, 447, 443; 514/859

[56] References Cited

U.S. PATENT DOCUMENTS

| | | | |
|---|---|---|---|
| D. 183,318 | 12/1939 | Fortunati | D24/147 |
| 227,362 | 5/1880 | Judson | 606/131 |
| 1,084,007 | 1/1914 | Hackett | 606/131 |
| 1,746,877 | 2/1930 | Tompkins | 132/333 |
| 1,965,861 | 7/1934 | Schneider | 606/131 |
| 2,361,506 | 10/1944 | Smith | 602/58 |
| 2,544,354 | 3/1951 | Reiter | 15/222 |
| 3,657,760 | 4/1972 | Kudisch | 424/443 |
| 3,720,205 | 3/1973 | Liebman | 15/222 |
| 3,910,284 | 10/1975 | Orentreich | 606/131 |
| 3,959,841 | 6/1976 | Horne | 15/222 |
| 4,438,767 | 3/1984 | Nelson | 606/131 |
| 4,459,987 | 7/1984 | Pangburn | 606/131 |
| 4,761,849 | 8/1988 | Taylor | 15/222 |
| 4,769,022 | 9/1988 | Chang | 606/131 |
| 4,891,228 | 1/1990 | Thaman | 424/443 |
| 5,035,523 | 7/1991 | Allinder | 15/222 |

Primary Examiner—Thurman K. Page
Assistant Examiner—Sally Gardner

[57] ABSTRACT

A facial cleanser comprises a narrow, thin, elongate strip that can be bent about its mid-point to form a bight portion and a pair of wing portions extending from the bight portion. The facial cleanser includes first and second opposed surfaces, the second surface being treated with an agent such as sunscreen, detergent, facial cream or an antiseptic. An alternative embodiment includes an absorbent pad for dispensing the skin-treating agent.

5 Claims, 1 Drawing Sheet

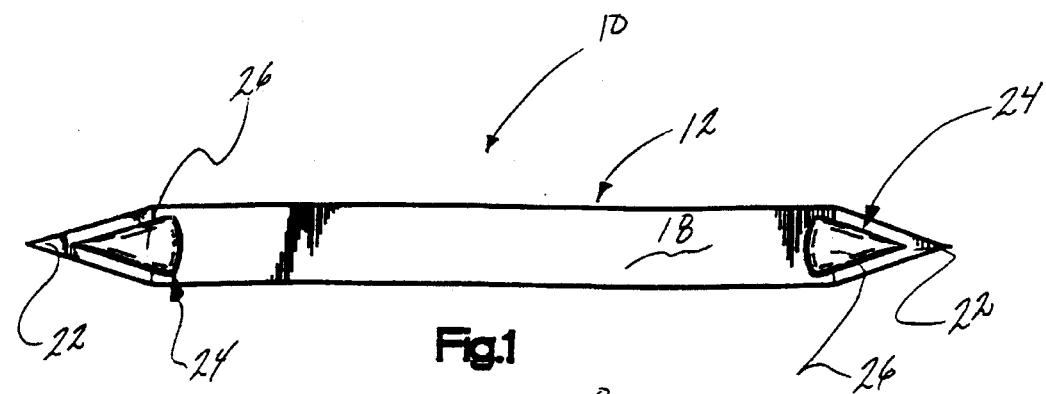
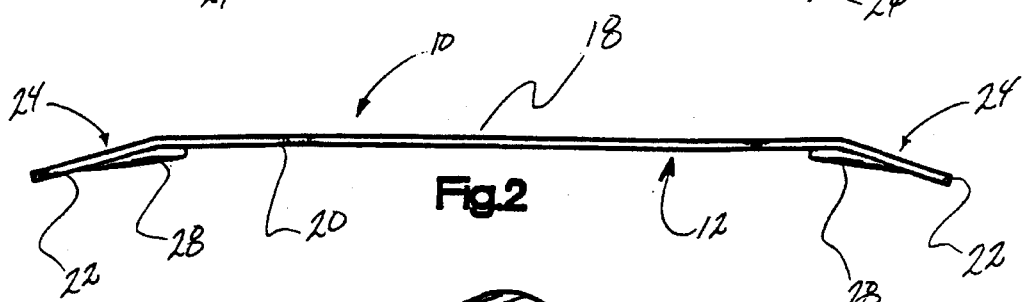
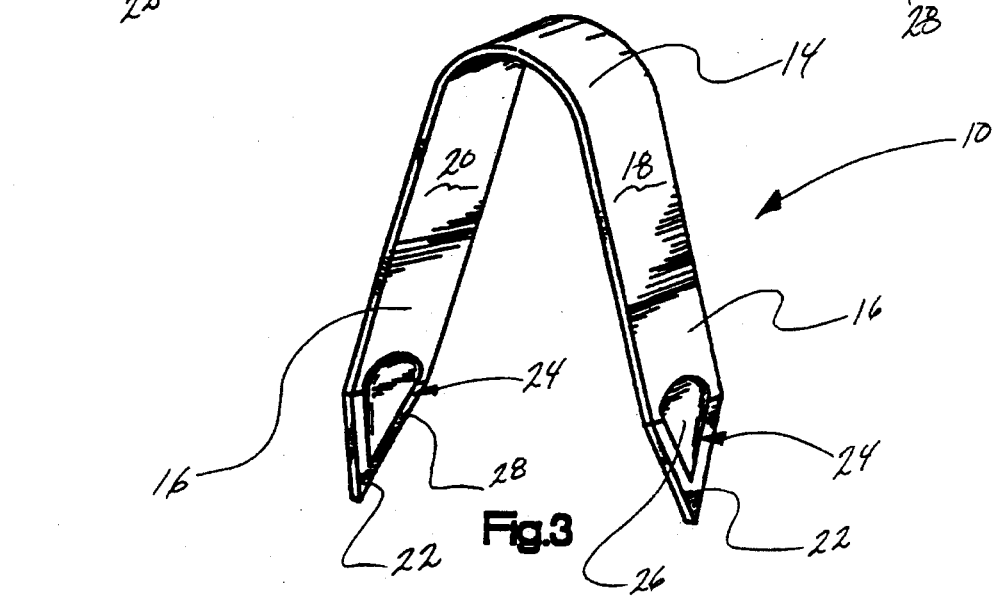
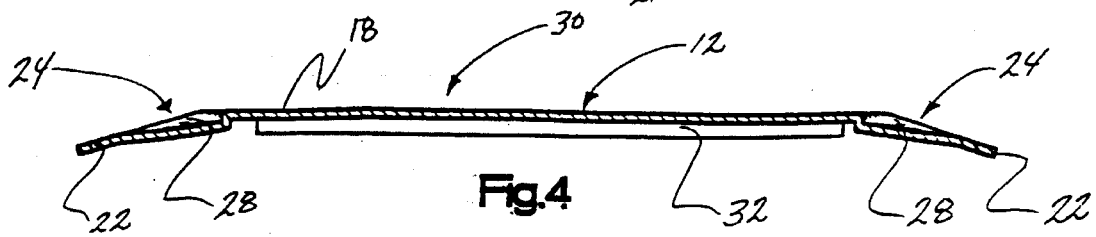

FACIAL CLEANSER

This application is a continuation of application Ser. No. 07/800,600, filed Nov. 27, 1991 abandoned.

BACKGROUND OF THE INVENTION

1. Field of the Invention

The present invention relates to a facial cleanser and, more particularly, to a scraper especially adapted for cleansing one's nose.

2. Description of the Prior Art

The concept of an appliance or device for use in scraping, abrading, rubbing, or otherwise removing accumulated sweat, dirt, or other debris from the human face is well known.

U.S. Pat. No. 1,084,007, issued Jan. 14, 1913, to G. E. Hackett, discloses a dermatological instrument for scraping and removing pus and sebaceous material from pimples. The Hackett instrument comprises a pair of elongate, tapered elements that converge to a point. A pimple is cleaned by placing the elements on either side of the pimple, applying pressure to the skin, and drawing the converging elements across the pimple.

A disadvantage of the Hackett instrument is its point-by-point method of cleansing pimples. That is, each pimple cleansed by the Hackett instrument must be cleansed individually. Ideally, an instrument would exist which would be able to cleanse an entire feature such as one's cheek or nose. Further, Hackett makes no mention of any antiseptic function performed by his instrument. Desirably, a facial cleansing device would nourish the skin at the same time that it cleanses the skin.

U.S. Pat. No. 1,965,861, issued Jul. 10, 1934, to R. S. Schneider, discloses a skin conditioner that employs a rigid, dished scraper plate attached to a handle. The plate has a convexly rounded edge that may be used to remove dirt and other material from the skin by manipulating the plate with the handle.

Although the Schneider device can cleanse larger areas of the skin than can the Hackett instrument, the Schneider device has certain disadvantages with respect to its use on facial projections such as one's nose. Since the Schneider device employs a rigid, solid plate, variations in nose shapes and sizes cannot be accommodated. Further, any indentations or other contour variations on the nose's surface would be passed over by Schneider's solid plate. As with the Hackett instrument, the Schneider device does not include any means for dispensing antiseptic agents or facial creams to repair damage to the skin that may be caused by rubbing or abrading of the skin.

Several patents have been issued for disc-like facial scrapers or cleansers. Specifically, U.S. Pat. No. 1,746,877, issued Feb. 11, 1930, to Tompkins, discloses a disc-like, celluoid facial cleanser. U.S. Pat. No. 4,438,767, issued Mar. 27, 1984 to Nelson, discloses an exfoliator disc that employs a flat, circular blade.

While the Tompkins and Nelson devices are more easily manipulated for use in the smaller crevasses and contours of the face than certain other facial cleansing devices, they share several disadvantages. Although both devices permit the user to grasp the respective devices close to the scraping edge, neither device can be used to cleanse the entire surface of one's nose. Rather, both the Tompkins and Nelson devices require the user to move from contour to contour on the nose's surface until the entire nose is clean. Such a procedure is tedious and time-consuming.

In view of the drawbacks of the prior art, a desirable facial cleanser would contact a larger portion of the surface to be cleaned, such as one's nose. Also, the cleanser desirably would be able to accommodate wide variations in the sizes and shapes of various noses. The device preferably would be compact and easy to use, while being inexpensive to manufacture. In addition, a desirable facial cleanser would be able to dispense antiseptic agents or facial creams that would nourish the skin while the skin is being cleansed.

SUMMARY OF THE INVENTION

In response to the foregoing concerns, the present invention provides a new and improved facial cleanser adapted for cleansing facial features such as one's nose that includes a narrow, thin, elongate strip that can be bent about its mid-point to form a bight portion and a pair of wing portions extending from the bight portion. The preferred facial cleanser is about 3.0 inches long, 1.0 inch wide and 0.27 inch thick.

The strip includes a first surface and an opposed second surface. The wing portions each include a means for gripping, said means for gripping being in the form of indentations in the first surface of each wing portion near the end thereof. The indentations may extend through the strip so as to form raised portions on the second surface.

If desired, the elongate strip can be treated with an agent that affects the skin being cleansed. The agent may be chosen from a wide variety of topical agents including facial creams, detergents, antiseptic agents such as benzoyl peroxide or alcohol, sunscreens and the like.

In an alternative embodiment, an absorbent pad is attached to the second surface of the strip, the pad being impregnated with an agent that affects the surface of the skin being cleansed. The agent may be the same agent as those mentioned above. The absorbent pad may be formed from any spongy material, such as sponge rubber, which is normally used in the application of makeup, facial creams and other topical skin agents.

The foregoing and other features and advantages of the invention are illustrated in the accompanying drawings and are described in more detail in the specification and claims that follow.

BRIEF DESCRIPTION OF THE DRAWINGS

FIG. 1 is a top plan view of a facial cleanser according to the invention;

FIG. 2 is a side elevational view of the facial cleanser of FIG. 1;

FIG. 3 is a perspective view of the facial cleanser of FIG. 1 in a bent position; and FIG. 4 is a side elevational view of an alternative embodiment of the facial cleanser showing an elongate pad attached to the facial cleanser.

DESCRIPTION OF THE PREFERRED EMBODIMENT

Referring to FIGS. 1–4, a facial cleanser is indicated generally by the reference numeral 10. The facial cleanser 10 is a narrow, thin, elongate strip 12 that can be bent about its midpoint to form a bight portion 14 and a pair of wing portions 16 extending from the bight portion 14. The facial cleanser 10 has a first surface 18 and an opposed second surface 20. The facial cleanser 10 is made of a planar, non-absorbent material suitable for scraping one's skin. The facial cleanser 10 preferably will be made of metal such as aluminum, but it can be made of hard rubber and polymers such as polyethylene, polypropylene and polyvinyl chloride, if desired. In its preferred form, the facial cleanser 10 will be about three inches long by one inch wide and will have a thickness of about 0.27 inch. It is expected that the cleanser 10 can be manufactured rapidly and inexpensively in a stamping or molding operation.

Each of the wing portions 16 includes a pointed end portion 22. Each end portion 22 is about 0.5 inch in length and is bent downwardly from the wing portion 16 as shown in FIG. 2. The facial cleanser 10 includes means for gripping the strip 12, said means for gripping being indicated by the reference numeral 24. Preferably, the means for gripping 24 is in the form of indentations 26 that are embossed or punched into the first surface 18 and which extend through the strip 12 so as to form raised portions 28 on the second surface 20.

If desired, the facial cleanser 10 may be treated with detergents, facial creams, sunscreens or antiseptic agents such as benzoyl peroxide or alcohol. Referring to FIG. 4, an alternative embodiment of the facial cleanser 10 is indicated by the reference numeral 30 and includes an absorbent pad 32 which may be used to dispense detergents, facial creams, sunscreens or antiseptic agents such as benzoyl peroxide or alcohol. Preferably, the pad 32 will be made of sponge rubber and will be attached to the second surface 20 as by gluing or ultrasonic welding.

OPERATION

If it is desired to cleanse one's nose, the user grasps the end portions 22 and bends the strip 12 into a shape such as that shown in FIG. 3. The bight portion 14 can be pressed against the bridge of the nose, while the wing portions 16 can be pressed against the sides of the nose. Thereafter, the strip 12 can be moved up and down along the nose while pressing the edges of the strip 12 firmly into the surface of the skin. Any accumulated oils, dirt, facial cream and so forth will be brought to the surface and scraped away. If the strip 12 has been treated with an agent such as a detergent, the cleansing action of the cleanser 10 will be enhanced. If the alternative embodiment 30 has been selected, the treating agent will be dispensed very effectively upon compression of the pad 32 during its movement along the surface of the skin.

As will be apparent from the foregoing description, the facial cleanser 10 can cover large areas of various facial surfaces. As a result, relatively few movements of the cleanser 10 are required to cleanse an entire facial surface such as one's nose. Further, the dimensions of the cleanser 10 are such that the cleanser 10 is light and easy to manipulate.

A further advantage of the facial cleanser 10 is that it is constructed from a single elongate strip. This construction makes the facial cleanser 10 easy to produce and reduces the cost of production. Also, since the facial cleanser 10 is inexpensive to produce, users may dispose of them as they are used. This reduces any chance of skin infections that might result from continued use of the same facial cleanser 10.

Another advantage of the facial cleanser 10 is that it is capable of dispensing antiseptic agents, facial creams or other skin products onto the surface of the skin as the facial cleanser 10 is drawn along the surface of the skin. Accordingly, the facial cleanser 10 is less damaging to the skin than other cleansing devices.

Although the invention has been described in its preferred form with a certain degree of particularity, it will be understood that the present disclosure of the preferred embodiment has been made only by way of example and that various changes may be resorted to without departing from the true spirit and scope of the invention as hereinafter claimed. It is intended that the patent shall cover, by suitable expression in the appended claims, whatever features of patentable novelty exist in the invention disclosed.

What is claimed is:

1. A facial cleanser adapted for cleansing a person's nose comprising:

an elongate strip having pointed ends and which is about 3.0 inches long, 1.0 inch wide and 0.27 inch thick and that can be bend about its mid-point to form a bight portion and a pair of wing portions extending from the bight portion, the strip being formed of a material suitable for scraping one's skin, said material being selected from the group consisting of polyethylene, polypropylene, polyvinyl chloride, metal and rubber;

the strip including a first surface and an opposed second surface;and gripping means for gripping the strip, the gripping means being disposed at the end of each wing portion, the gripping means being in the form of indentations in the first surface that extend through the strip so as to form raised portions on the second surface; and an absorbent pad attached to the second surface of said strip, the pad being impregnated with a topically effective agent for application to the surface of the skin being cleansed.

2. The facial cleanser of claim 1, wherein the agent is an antiseptic selected from the group consisting of benzoyl peroxide and alcohol.

3. The facial cleanser of claim 1, wherein the agent is a detergent.

4. The facial cleanser of claim 1, wherein the agent is a facial cream.

5. The facial cleanser of claim 1, wherein the elongate pad is made of sponge rubber.

* * * * *